(12) United States Patent
Zhang et al.

(10) Patent No.: US 10,041,118 B2
(45) Date of Patent: Aug. 7, 2018

(54) METHOD FOR ANALYZING WATER TOXICITY

(71) Applicant: Nanjing University, Nanjing (CN)

(72) Inventors: Yan Zhang, Nanjing (CN); Hongqiang Ren, Nanjing (CN); Bing Wu, Nanjing (CN); Xuxiang Zhang, Nanjing (CN)

(73) Assignee: NANJING UNIVERSITY, Nanjing (CN)

( * ) Notice: Subject to any disclaimer, the term of this patent is extended or adjusted under 35 U.S.C. 154(b) by 894 days.

(21) Appl. No.: 14/476,709

(22) Filed: Sep. 3, 2014

(65) Prior Publication Data

US 2015/0141271 A1 May 21, 2015

(30) Foreign Application Priority Data

Nov. 15, 2013 (CN) .......................... 2013 1 0574746

(51) Int. Cl.
| | |
|---|---|
| *G01N 33/18* | (2006.01) |
| *C12Q 1/6883* | (2018.01) |
| *G01N 33/50* | (2006.01) |
| *G01N 24/08* | (2006.01) |
| *G06F 19/20* | (2011.01) |

(52) U.S. Cl.
CPC ......... *C12Q 1/6883* (2013.01); *G01N 24/088* (2013.01); *G01N 33/18* (2013.01); *G01N 33/186* (2013.01); *G01N 33/1813* (2013.01); *G01N 33/50* (2013.01); *G06F 19/20* (2013.01); *C12Q 2600/142* (2013.01); *C12Q 2600/158* (2013.01); *G01N 2570/00* (2013.01)

(58) Field of Classification Search
None
See application file for complete search history.

(56) References Cited

U.S. PATENT DOCUMENTS

| | | | |
|---|---|---|---|
| 7,415,358 B2* | 8/2008 | Mendrick ............ | C12Q 1/6883 435/6.16 |
| 2002/0001825 A1 | 1/2002 | Itoh | |
| 2004/0072723 A1 | 4/2004 | Palsson et al. | |
| 2006/0143718 A1* | 6/2006 | Nebert ................. | G01N 21/763 800/3 |
| 2007/0003965 A1 | 1/2007 | Ramsay et al. | |
| 2013/0259847 A1 | 10/2013 | Vishnudas et al. | |

FOREIGN PATENT DOCUMENTS

| | | |
|---|---|---|
| CN | 101813680 A | 8/2010 |
| CN | 102323285 A | 1/2012 |
| WO | 2009113044 A2 | 9/2009 |
| WO | 2013113921 A1 | 8/2013 |

OTHER PUBLICATIONS

Choe et al., Preferred analysis methods for Affymetrix GeneChips revealed by a wholly defined control dataset. Genome Biology 2005, 6:R16.*
Vitols et al., Identifying and Quantifying Metabolites in Blood Serum and Plasma. Chenomx Corp. Application Notes. Jun. 2006, pp. 1-6.*
Cho et al., Discovery of metabolite features for the modelling and analysis of high-resolution NMR spectra. Int J Data Min Bioinform. 2008 ; 2(2): 176-192.*
Cui et al., Use of transcriptomics in understanding mechanisms of druginduced toxicity. Pharmacogenomics. Apr. 2010 ; 11(4): 573-585.*
Tulpan et al., MetaboHunter: an automatic approach for identification of metabolites from 1H-NMR spectra of complex mixtures. BMC Bioinformatics 2011, 12:400-422.*
Xia et al., Web-based inference of biological patterns, functions and pathways from metabolomic data using MetaboAnalyst.Nature Protocols, 2011, 6:743-760.*
Wang et al., Urine Metabolomics Analysis for Biomarker Discovery and Detection of Jaundice Syndrome in Patients With Liver Disease. Molecular & Cellular Proteomics. 2012 11:370-380.*
Zhang et al., Evaluation of the Toxic Effects of Municipal Wastewater Effluent on Mice Using Omic Approaches. Environ. Sci. Technol. 2013, 47, 9470-9477.*
Zhang et al., Characterisation of acute toxicity, genotoxicity and oxidative stress posed by textile effluent on zebrafish. Journal of Environmental Sciences 2012, 24(11) 2019-2027. (Year: 2012).*
Y. Zhang et al., Evaluation of the toxic effects of municipal wastewater effluent on mice using omic approaches, Environmental Science & Technology, Jul. 24, 2013, pp. 9470-9477, vol. 47, American Chemical Society, United States.
Y. Zhang et al., Supporting information: Evaluation of the toxic effects of municipal wastewater effluent on mice using omic approaches, Environmental Science & Technology, Jul. 24, 2013, pp. S1-S16, American Chemical Society, United States.

\* cited by examiner

*Primary Examiner* — Kevin K Hill
*Assistant Examiner* — Arthur S Leonard
(74) *Attorney, Agent, or Firm* — Matthias Scholl, PC; Matthias Scholl

(57) ABSTRACT

A method for analyzing water toxicity, the method including: exposure experiment, sample collection, transcriptome detection, metabolome detection, screening of differentially expressed genes, screening of differentially expressed metabolites, and identification of commonly changed biological pathways in both the transcriptome and the metabolome.

3 Claims, 3 Drawing Sheets

METHOD FOR ANALYZING WATER TOXICITY

CROSS-REFERENCE TO RELATED APPLICATIONS

Pursuant to 35 U.S.C. § 119 and the Paris Convention Treaty, this application claims the benefit of Chinese Patent Application No. 201310574746.9 filed Nov. 15, 2013, the contents of which are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, Mass. 02142.

BACKGROUND OF THE INVENTION

Field of the Invention

The invention relates to a method for water toxicity assessment, and more particularly to a method for analyzing water toxicity based on bio-omics integration technology, specifically, to a high throughput screening method for comprehensively analyzing complicate water toxicity and toxicity mechanism thereof based on bio-omics integration technology.

Description of the Related Art

Trace toxic and hazardous organic pollutants and heavy metals have been detected in secondary effluent from sewage treatment plants, sources of drinking water, and tap water. Such pollutants cause environmental health risks. Thus, it is desired to develop a comprehensive, accurate, and sensitive method for analyzing water toxicity to determine the effect and mechanism of sewage toxicity and to predict risks to human health.

Conventional water toxicity assessment methods include bioassays based on in vitro and in vivo detection. These detection methods use biological reaction endpoints (such as death rates, stress responses, and oxidative damages) to reflect toxicity effects of pollutants, which are simple and fast. However, such conventional methods have the following disadvantages: 1) The conventional methods only reflect individual biochemical functions and states of organism or tissue and organ, and lack entire and systematic toxicity assessment indexes. 2) Such methods are not sensitive enough; they are only responsive to pollutants of high concentrations but unable to detect the toxicity effect of trace pollutants. 3) Because pollutants are complex, it is difficult to identify and detect each component, and it is unrealistic to conduct biological toxicity detection for each component. Besides, joint toxicity, including synergistic or antagonistic effects, may occur between different pollutants. All of the above make it difficult to accurately assess the comprehensive toxicity and toxicity mechanism of the water body using conventional methods.

SUMMARY OF THE INVENTION

In view of the above-described problems, it is one objective of the invention to provide a method for analyzing water toxicity.

The method is based on integration of transcriptomics and metabolomics and is capable of conducting high throughput assay on complicate toxicity and toxicity mechanism of the polluted water and comprehensively and accurately providing parameters and indexes of biological information.

To achieve the above objective, in accordance with one embodiment of the invention, there is provided a method for analyzing water toxicity. The method comprises the following steps:

1) exposure experiment: using polluted water as a water sample to be tested and a purified water as a blank control group; selecting model animals (model animals having complete genetic information, such as zebrafishes (*Danio rerio*), mice, and rats,) for conducting the exposure experiment, with 10 model animals in each group;

2) sample collection: after a cycle of the exposure experiment, extracting total RNA samples of livers; collecting blood, centrifuging the blood at a rotational speed of 3000 rpm for 20 min to obtain serum samples;

3) transcriptome detection: mixing every three RNA samples to yield one sample, conducting transcriptome microarray detection, in which, the microarray is gene chip Mouse Genome 430A 2.0 array produced by Affymetrix Company in the USA; providing three gene chips for the experimental group and the blank control group, respectively; and conducting statistics analysis, whereby obtaining complete genome expression data of model animals;

4) metabolome detection: collecting 300 μL of a serum sample from each test animal of the experimental group and the blank control group; adding 300 μL of a phosphate buffer having a pH value of 7.4 to each serum sample and evenly mixing to yield a mixture; collecting 550 μL of a supernate from the mixture; and conducting nuclear magnetic resonance (NMR) detection on the supernate by using Bruker AV600 NMR apparatus produced by Bruker Company in Germany;

5) screening of differentially expressed genes: comparing gene expression signals of the experimental group with the gene expression signals of the blank control group according to detection results of the gene chips; screening genes having an expression multiple >2.0 and a false discovery rate (FDR)<0.1 as the differentially expressed genes, the standard of which not only eliminates disturbance of false-positive signal of the gene chip is eliminated, but also screens a sufficiently large number of differentially expressed genes from ten thousands of complete genomes for subsequent analysis of biological pathway;

6) screening of differentially expressed metabolites: performing segmental integral on NMR spectra of serum with an interval of 0.005 ppm, the standard of which is capable of improving identification resolution of spectral peaks of serum metabolites and decreasing errors resulting from overlapping peaks; conducting partial least squares discriminant analysis (PLS-DA) on obtained integral data using a multivariate data analysis software SIMCA-P 11.5 (produced by Umetrics Company in the USA); and selecting metabolites having variable influence on projection (VIP) >1.0 and FDR <0.01 as the differentially expressed metabolites, which not only have significant variations in both the experimental group and the blank control group but also have large contribution to the PLS-DA model; and 7) identification of biological pathways: analyzing biological pathways of the differentially expressed genes using Gene Ontology (GO) and Kyoto Encyclopedia of Genes and Genomes (KEGG), and identifying pathways that contains more than four differentially expressed genes and has a hypergeometric test p <0.05 as pathways obviously affected based on the transcriptomes; analyzing biological pathways of differentially expressed metabolites using MetaboAnalyst 2.0, and identifying pathways having a pathway impact (PI) >0.1 as pathways obviously affected based on the metabolites; and screening biological pathways where both the transcriptome and the metabolome are affected. The finally identified biological pathways indicate specific biological processes in the organisms that are affected by the toxicity of the test water sample, such as oxidative stress, metabolic disorders, and liver toxicity.

The toxicity effect can be demonstrated by other biological methods, respectively, but the method of the invention is capable of simultaneously detecting a plurality of complicate toxicities of the test water sample.

Corresponding differentially expressed genes and the metabolites can be used as biomarkers to judge the water toxicity.

Advantages according to embodiments of the invention are summarized as follows:

Based on the integration of the transcriptome and the metabolome, the method of the invention comprehensively and accurately assesses complicate toxicity of the water from the biological underlying genetic information to the final phenotype. The method of the invention overcomes drawbacks of the existing assessment method and screens the new type biomarker for identifying the complicate toxicity effect. Thus, the integration of different bio-omics is simple and effectively, and the processing of high-throughput bioinformatics data is largely simplified. The method has obvious effect on the toxicity detection of the micro-polluted water, even toxicity of water having pollutant concentrations of nanogram level. While the conventional toxicity assessment method is only responsive to pollutants with concentrations of milligram level or above.

BRIEF DESCRIPTION OF THE DRAWINGS

The invention is described hereinbelow with reference to the accompanying drawings, in which.

DETAILED DESCRIPTION OF THE EMBODIMENTS

For further illustrating the invention, experiments detailing a method for analyzing water toxicity based on bio-omics integration are described below. It should be noted that the following examples are intended to describe and not to limit the invention.

EXAMPLE 1

Figure 1:
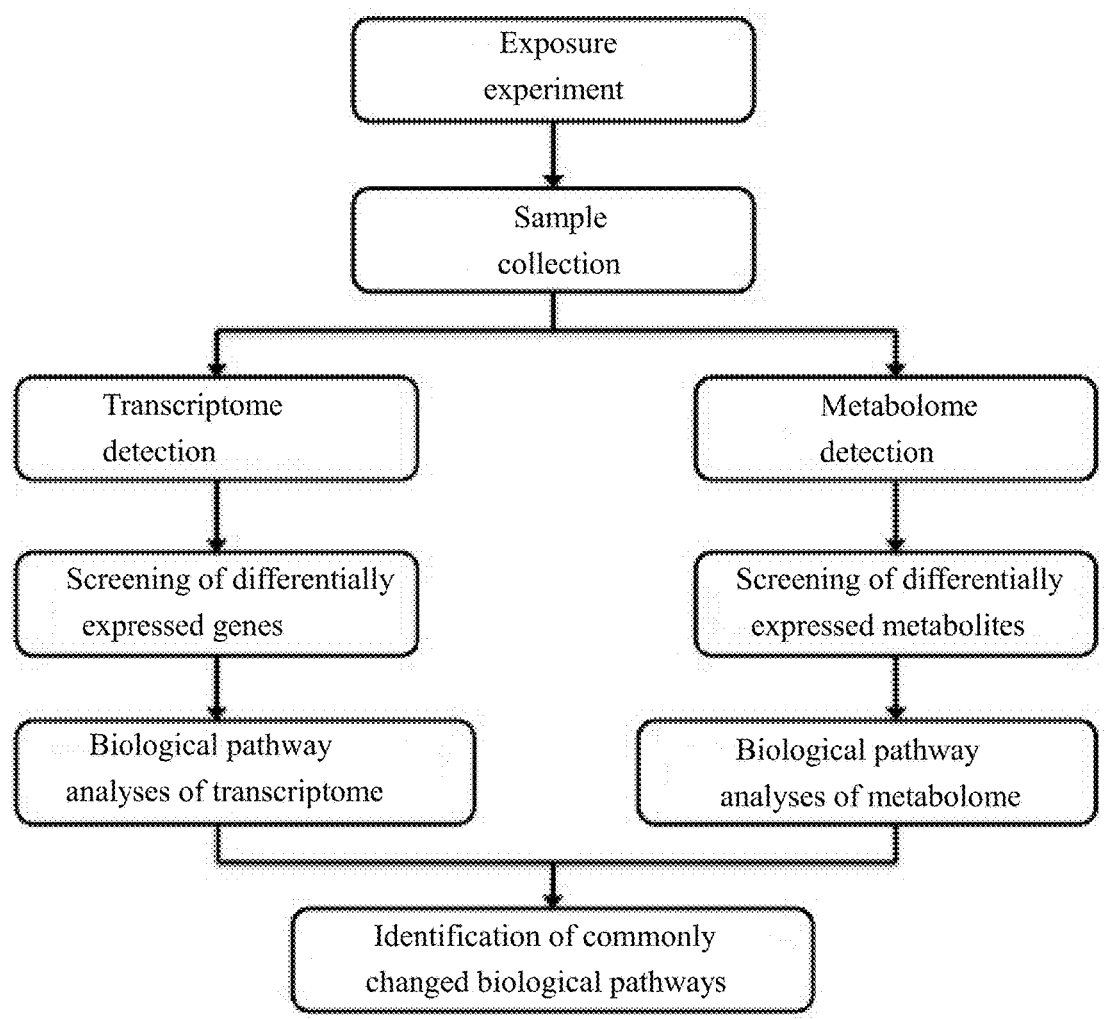
FIG. 1 is a flow chart of a method for analyzing water toxicity in accordance with one embodiment of the invention.

A method for analyzing water toxicity based on bio-omics integration, to assess the toxicity of micro-polluted drinking water source, as shown in FIG. 1, is conducted as follows:

1) Exposure experiment: a sample of drinking water source and a sample of purified water were administered to mice by freely drinking. The test mice were seven weeks old male Kunming mice (*Mus musculus*) having and a weight of between 17 and 31 g and were randomly divided into an experimental group and a control group with ten in each group. The mice were administered with the water sample of the drinking water source and the sample of the purified water. An exposure period was 90 days.

2) Sample collection: after 90 days of the exposure period, total RNA samples of livers were extracted from the experimental group and the control group, and serum samples were collected.

3) transcriptome detection: mice genome chip Mouse Genome 430A 2.0 produced by Affymetrix Company from the USA were used for the transcriptome detection. The experimental group and the control group were provided with three genome chips, respectively. Statics analyses were conducted, and the complete genome expression data of the test mice were obtained.

4) Metabolome detection: 300 μL of the serum sample was collected from each mouse in the experimental group and the control group. 300 μL of a phosphate buffer having a pH value of 7.4 was added to each serum sample and evenly mixed to yield a mixture. 550 μL of a supernate was collected from the mixture and was performed with nuclear magnetic resonance (NMR) detection. Segmental integral was performed on the NMR spectra of serum (with an interval of 0.005 ppm), and the integral data were input into the multivariate data analysis software SIMCA-P 11.5 to establish a PLS-DA model.

5) Screening of differentially expressed genes: genes having an expression multiple >2.0 and a false discovery rate (FDR)<0.1 were screened as the differentially expressed genes, and 243 differentially expressed genes were screened from ten thousands of complete genomes of the experimental group.

6) Screening of differentially expressed genes: metabolites having the variable influence on projection (VIP) >1.0 and FDR <0.01 were screened as the differentially expressed metabolites, and 10 differentially expressed metabolites were screened from thousands of the experimental group.

7) Biological pathway analyses were performed on the differentially expressed genes and metabolites, respectively, and three biological pathways where both the transcriptomes and the metabolites are affected (as shown in Table 1).

TABLE 1

Biological pathways of mice obviously affected by toxicity of drinking water

| Screening of differentially expressed genes | | | Screening of differentially expressed metabolites | | | Commonly changed biological pathways | | | |
|---|---|---|---|---|---|---|---|---|---|
| Genes | FDR | Expression times | Metabolite | FDR | Variable Influence on Projection (VIP) | Pathways | Number of differentially expressed genes | Hypergeometric Test p | Pathway Impact PI |
| Adh4 | 0.050 | 2.0 | Glutathione | 0.005 | 1.1 | Exogenous substances metabolic pathways involving cytochrome P450 | 6 | 0.005 | 0.15 |
| Cyp1a1 | 0.004 | 2.2 | Glutamine | 0.004 | 1.2 | | | | |
| Cyp2b10 | 0.041 | 2.9 | | | | | | | |
| Cyp2c55 | 0.003 | 5.7 | | | | | | | |
| Cyp2c65 | 0.040 | 3.9 | | | | | | | |
| Gstm4 | 0.005 | 2.3 | | | | | | | |
| Adh4 | 0.050 | 2.0 | Choline | 0.007 | 1.2 | Bile acid biological pathway | 4 | 0.004 | 0.15 |
| Akr1d1 | 0.035 | −2.0 | Trimethylamine N-oxide | 0.005 | 1.3 | | | | |
| Cyp7a1 | 0.005 | −3.0 | Taurine | 0.004 | 1.5 | | | | |
| Hsd3b7 | 0.040 | 2.0 | Pyruvic acid | 0.003 | 1.4 | | | | |
| | | | Citric acid | 0.001 | 1.3 | | | | |
| | | | Lipid | 0.006 | 1.1 | | | | |
| Acs14 | 0.050 | −2.0 | Cholesterol | 0.004 | 1.6 | PPAR Signaling Pathway | 5 | 0.005 | 0.19 |
| Cyp7a1 | 0.005 | −3.0 | Lipid | 0.006 | 1.1 | | | | |
| Fabp2 | 0.025 | 2.0 | | | | | | | |
| Hmgcs2 | 0.003 | 2.2 | | | | | | | |
| Sorbs1 | 0.006 | 2.0 | | | | | | | |

These three biological pathways comprised: cytochrome P450 involved in the metabolic pathway of exogenous substance (involving 6 differentially expressed proteins and 2 differentially expressed serum metabolites), biosynthetic pathway of fatty acid (involving 4 differentially expressed genes and 6 differentially expressed serum metabolites), and PPAR signal pathway (involving 5 differentially expressed genes and 2 differentially expressed serum metabolites).

The toxicity effect of the test micro-polluted drinking water source primarily affects the metabolic pathway of the exogenous substance and the metabolic process of fatty acid, and the micro-polluted drinking water source results in liver damage and metabolic disorder of the mice. The finally screened differentially expressed genes and the serum metabolites can be used as potential biomarkers of the toxicity of the micro-polluted drinking water source.

It has been found that 14 of 16 representative pollutants in the test water have concentrations of a nanogram level (as shown in Table 2), to which the conventional toxicity assessment methods were not responsive.

TABLE 2

Concentration test results of representative pollutants in slightly-polluted drinking water (Unit: ng/L, Mean ± standard deviation, each target is tested thrice)

| Pollutant | Concentration | Pollutant | Concentration |
|---|---|---|---|
| Isophorone | 11 ± 2 | Benzo (a) anthracene | 15 ± 2 |
| Dimethyl phthalate | 79 ± 8 | Phthalate-di (2-ethylhexyl) ester | 1820 ± 281 |
| Chrysene | 31 ± 4 | Benzo (b) fluoranthene | 161 ± 17 |
| Anthracene | 96 ± 4 | Benzo (k) fluoranthene | 99 ± 12 |
| Phenanthrene | 19 ± 1 | Benzo (a) pyrene | 195 ± 14 |
| 2-n-butyl phthalate | 3391 ± 1265 | Benzo (g, h, i) perylene | 2 ± 1 |
| Pyrene | 14 ± 6 | Indeno (1,2,3-cd) pyrene | 13 ± 12 |
| Bis (2-ethylhexyl) adipate | 206 ± 84 | Dibenzo (a, h) anthracene | 5 ± 2 |

Figure 2A:
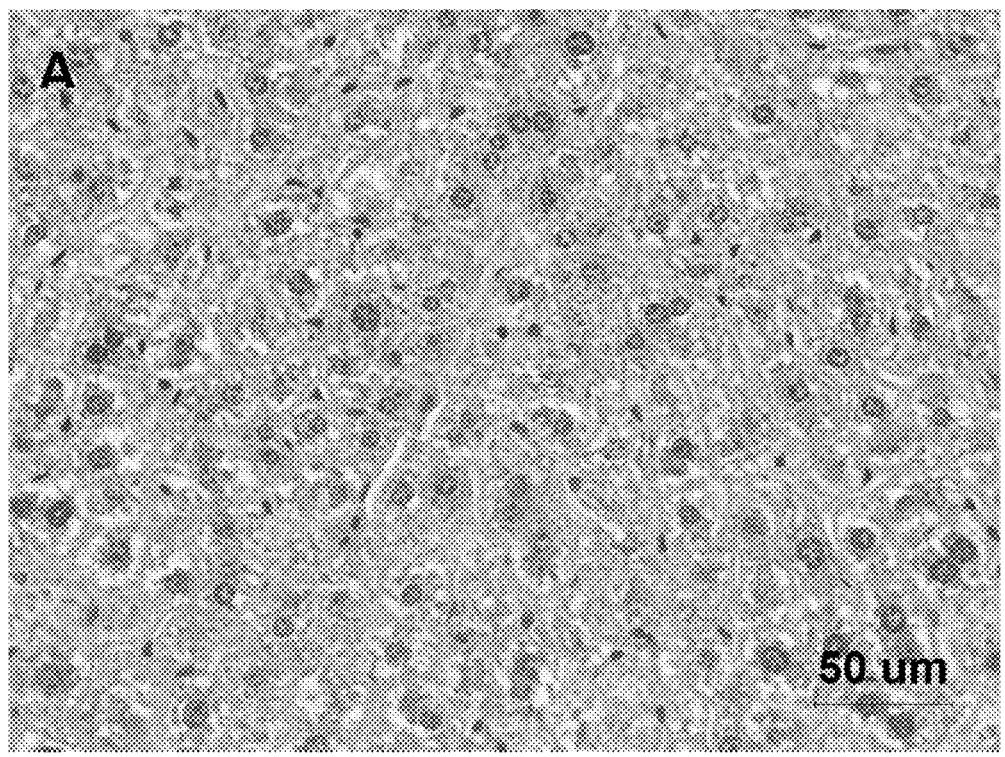
FIG. 2A is a picture showing detection result of a tissue section of liver in a blank control group in accordance with one embodiment of the invention.
Figure 2B:
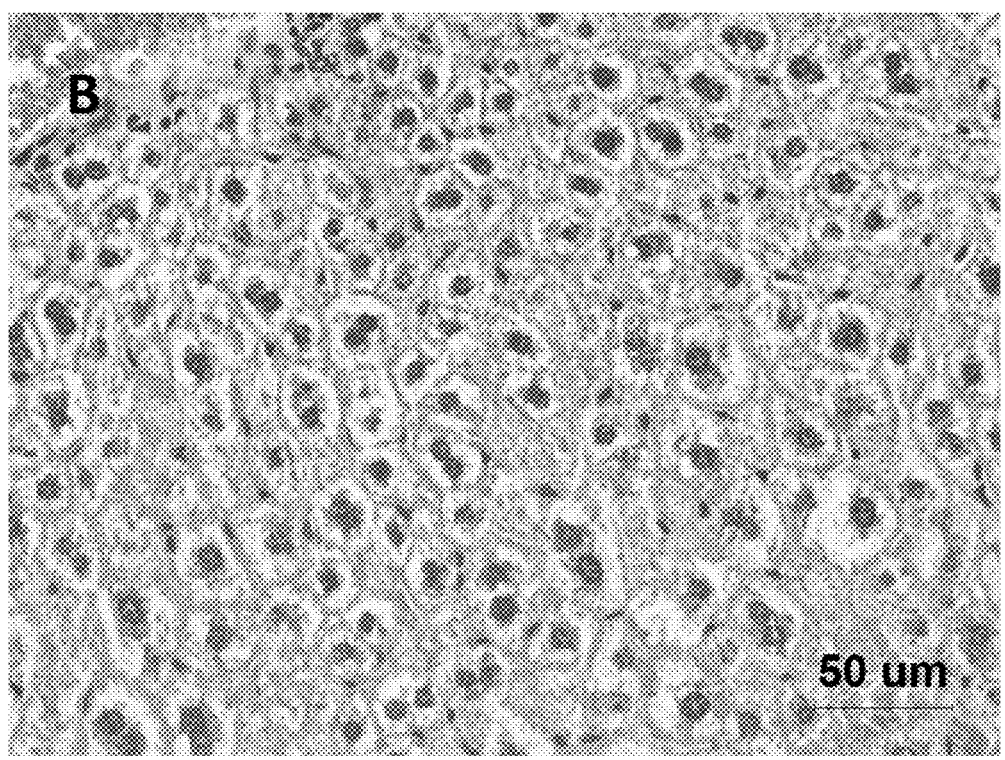
FIG. 2B is a picture showing detection result of a tissue section of liver in an experimental group in accordance with one embodiment of the invention.
Figure 3A:
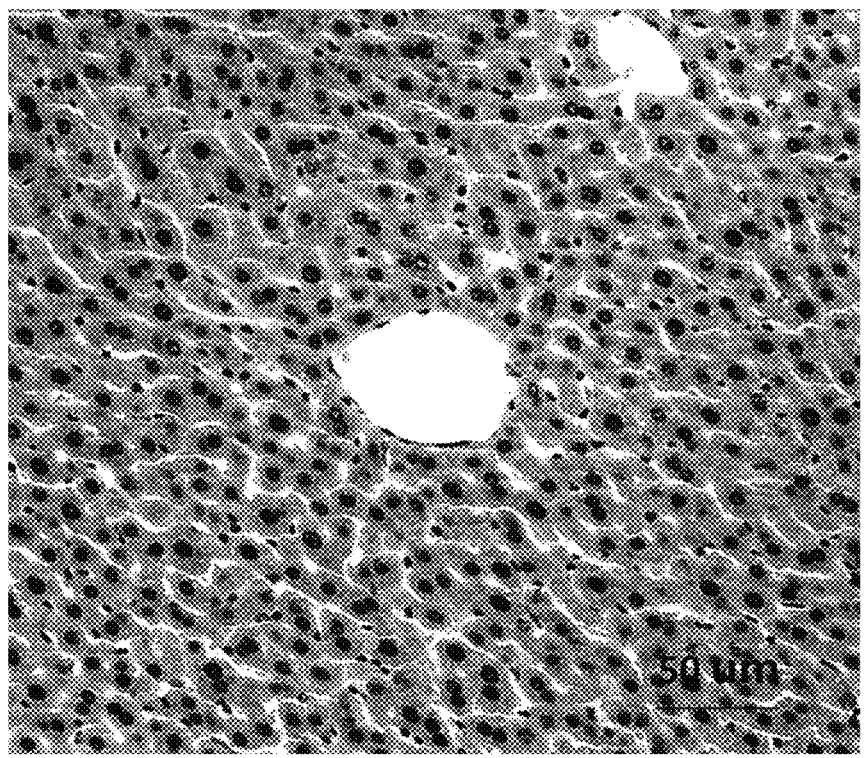
FIG. 3A is a picture showing detection result of a tissue section of liver in a blank control group in accordance with one embodiment of the invention.
Figure 3B:
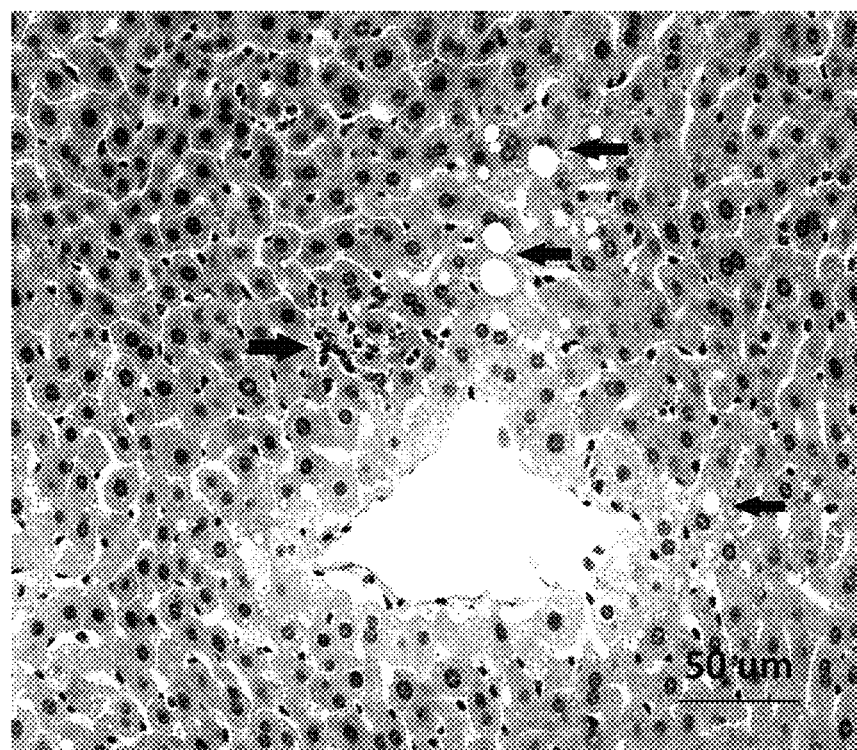
FIG. 3B is a picture showing detection result of a tissue section of liver in an experimental group in accordance with one embodiment of the invention.

Histopathological test results did not find that the micro-polluted water source resulted in liver lesions (FIG. 2), and test results of 14 serum biochemical indicator did not find that the test water led to changes in serum pathological indicators (Table 3).

TABLE 3

Biochemical test results of serum (Mean ± standard deviation, 10 animals/group)

| Biochemical parameters of serum | Blank control group | Experimental group |
|---|---|---|
| Total protein (g/L) | 55.3 ± 4.0 | 56.0 ± 3.5 |
| Albumin (g/L) | 29.3 ± 2.1 | 30.1 ± 1.2 |
| Globulin (g/L) | 26.0 ± 2.6 | 26.0 ± 2.9 |
| Glutamic-pyruvic transaminase (U/L) | 95.5 ± 40.2 | 168.6 ± 162.9 |
| Glutamic-oxal(o)acetic transaminase (U/L) | 135 ± 28 | 200 ± 127 |
| Alkaline phosphatase (U/L) | 56 ± 21 | 52 ± 20 |
| Lactate dehydrogenase (U/L) | 728 ± 286 | 895 ± 442 |
| Blood urea nitrogen (μmol/L) | 7.3 ± 0.7 | 7.8 ± 1.1 |
| Creatinine (μmol/L) | 23 ± 2 | 23 ± 4 |
| Uric acid (μmol/L) | 116 ± 37 | 78 ± 26[b] |
| Cholesterol (mmol/L) | 2.81 ± 0.39 | 2.92 ± 0.42 |
| Triglyceride (mmol/L) | 3.19 ± 1.10 | 4.52 ± 2.16 |
| High-density lipoprotein cholesterol (mmol/L) | 1.89 ± 0.21 | 1.88 ± 0.25 |
| Low-density lipoprotein cholesterol (mmol/L) | 0.56 ± 0.12 | 0.61 ± 0.15 |

The method of the invention was capable of simultaneously detecting a plurality of toxicity effects of the micro-polluted water source on the liver damage and the metabolic disorder, thereby having high sensitivity and obvious advantage.

EXAMPLE 2

A method for analyzing water toxicity based on bio-omics integration, to assess the toxicity of secondary effluent from a municipal sewage treatment plant is conducted as follows:

1) Exposure experiment: a sample of the effluent of the sewage treatment plant and a sample of purified water were administered to mice by freely drinking. The test mice were seven weeks old male kunming mice (*Mus musculus*) having a weight of between 18 and 25 g and were randomly divided into an experimental group and a control group with ten in each group. The mice were administered with the water sample of the drinking water source and the sample of the purified water. An exposure period was 90 days.

2) Sample collection: after 90 days of the exposure period, total RNA samples of livers were extracted from the experimental group and the control group, and serum samples were collected.

genes, and 767 differentially expressed genes were screened from ten thousands of complete genomes of the experimental group.

6) Screening of differentially expressed genes: metabolites having the variable influence on projection (VIP) >1.0 and FDR <0.01 were screened as the differentially expressed metabolites, and 5 differentially expressed metabolites were screened from thousands of the experimental group.

7) Biological pathway analyses were performed on the differentially expressed genes and metabolites, respectively, and three biological pathways where both the transcriptomes and the metabolites are affected (as shown in Table 4).

TABLE 4

Biological pathways of mice obviously affected by toxicity of secondary effluent from sewage treatment plant

| Screening of differentially expressed genes | | | Screening of differentially expressed metabolites | | | Commonly changed biological pathways | | | |
|---|---|---|---|---|---|---|---|---|---|
| Genes | FDR | Expression times | Metabolite | FDR | Variable Influence on Projection (VIP) | Pathways | Number of differentially expressed genes | Hypergeometric Test p | Pathway Impact PI |
| Cyp51 | 0.033 | −4.1 | Choline | 0.004 | 1.5 | Steroid biosynthesis | 7 | 0.004 | 0.14 |
| Ggcx | 0.052 | −3.3 | Phosphocholine | 0.003 | 1.7 | | | | |
| Hmgcr | 0.005 | −3.2 | | | | | | | |
| Lss | 0.045 | −3.8 | | | | | | | |
| Sc4mo1 | 0.007 | −3.3 | | | | | | | |
| Sq1e | 0.035 | −3.6 | | | | | | | |
| Tm7sf2 | 0.050 | −3.1 | | | | | | | |
| Acy3 | 0.008 | −3.8 | Proline | 0.005 | 1.9 | Metabolism of alanine, aspartic acid and glutamic acid | 4 | 0.005 | 0.15 |
| Asns | 0.054 | −3.1 | | | | | | | |
| Aspa | 0.034 | −3.6 | | | | | | | |
| Ddo | 0.009 | −3.9 | | | | | | | |
| Atp6v1c1 | 0.010 | −3.3 | 2-oxoglutaric acid | 0.001 | 1.2 | Oxidation phosphorylation | 6 | 0.003 | 0.17 |
| Cox4i1 | 0.075 | −3.1 | Lactic acid | 0.004 | 1.4 | | | | |
| Cox5a | 0.050 | −3.2 | | | | | | | |
| Cox5b | 0.004 | −3.0 | | | | | | | |
| Ndufa2 | 0.065 | −4.1 | | | | | | | |
| Ndufc1 | 0.074 | −3.6 | | | | | | | |

3) transcriptome detection: mice genome chip Mouse Genome 430A 2.0 produced by Affymetrix Company from the USA were used for the transcriptome detection. The experimental group and the control group were provided with three genome chips, respectively. Statics analyses were conducted, and the complete genome expression data of the test mice were obtained.

4) Metabolome detection: 300 μL of the serum sample was collected from each mouse in the experimental group and the control group. 300 μL of a phosphate buffer having a pH value of 7.4 was added to each serum sample and evenly mixed to yield a mixture. 550 μL of a supernate was collected from the mixture and was performed with nuclear magnetic resonance (NMR) detection. Segmental integral was performed on the NMR spectra of serum (with an interval of 0.005 ppm), and the integral data were input into the multivariate data analysis software SIMCA-P 11.5 to establish a PLS-DA model.

5) Screening of differentially expressed genes: genes having an expression multiple >2.0 and a false discovery rate (FDR)<0.1 were screened as the differentially expressed These three biological pathways comprised: biosynthetic pathways of steroid hormone (involving 7 differentially expressed genes and 2 differentially expressed serum metabolites), Alanine, Aspartic acid, and Glutamate (involving 4 differentially expressed genes and 1 differentially expressed serum metabolite), and oxidative phosphorylation pathway (involving 6 differentially expressed genes and 2 differentially expressed serum metabolites).

The toxicity effect of the test secondary effluent from the sewage treatment plant primarily affects the fat metabolism, amino acid metabolism, and energy metabolism. The secondary effluent of the sewage treatment plant has toxicity effects on the normal liver functions including metabolisms of fat, amino acid, and energy. The differentially expressed genes and the serum metabolites from the screening process can be used as potential biomarkers of the toxicity of the secondary effluent from the sewage treatment plant.

It has been found that 13 trace organic pollutants were detected from 22 representative pollutants in the test water and had concentrations of a nanogram level (as shown in Table 5), to which the conventional toxicity assessment methods were not responsive.

TABLE 5

Concentration test results of representative pollutants in slightly-polluted drinking water (Unit: ng/L, Mean ± standard deviation, each target is tested thrice)

| Pollutant | Concentration | Pollutant | Concentration |
|---|---|---|---|
| Acenaphthene | 10.22 ± 0.06 | Phenanthrene | 22.93 ± 0.17 |
| Anthracene | 26.16 ± 1.82 | Pyrene | 3.69 ± 0.37 |
| Benzo (a) anthracene | Undetected | Butyl benzyl phthalate | 149.33 ± 6.45 |
| Benzo (a) pyrene | Undetected | Dioctyladipate | 77.57 ± 1.37 |
| Benzo (b) Fluoranthene | Undetected | Phthalate-di (2-ethylhexyl) phthalate | 77.26 ± 0.13 |
| Benzo (g, h, i) Perylene | Undetected | Diethyl phthalate | 39.25 ± 1.08 |
| Benzo (k) Fluoranthene | 28.73 ± 0.41 | Dimethyl phthalate | 51.73 ± 1.46 |
| Chrysene | 62.23 ± 0.01 | 2-n-butyl phthalate | 71.03 ± 8.52 |
| Dibenzo (a, h) Anthracene | Undetected | Hexachlorobenzene | Undetected |
| Fluorene | Undetected | Hexachlorocyclopentadiene | Undetected |
| Indeno (1,2,3-cd) Pyrene | Undetected | Pentachlorophenol | 421.06 ± 1.70 |

Histopathological test results did not find that the secondary effluent of the sewage treatment plant resulted in liver lesions (FIG. 2), and test results of 14 serum biochemical indicator did not find that the test water sample led to changes in serum pathological indicators (Table 6).

TABLE 6

Biochemical test results of serum (Mean ± standard deviation, 10 animals/group)

| Biochemical parameters of serum | Blank control group | Experimental group |
|---|---|---|
| Total protein (g/L) | 62.5 ± 3.0 | 62.9 ± 4.1 |
| Albumin (g/L) | 29.9 ± 2.5 | 29.1 ± 2.2 |
| Globulin (g/L) | 30.9 ± 1.4 | 33.7 ± 3.8 |
| Glutamic-pyruvic transaminase (U/L) | 59.7 ± 4.6 | 57.0 ± 8.0 |
| Glutamic-oxal(o)acetic transaminase (U/L) | 113.7 ± 8.1 | 116.0 ± 5.0 |
| Alkaline phosphatase (U/L) | 43.1 ± 9.9 | 56.0 ± 9.0 |
| Lactate dehydrogenase (U/L) | 625.8 ± 144.2 | 665.3 ± 165.8 |
| Blood urea nitrogen (mmol/L) | 8.7 ± 1.4 | 8.4 ± 1.1 |
| Creatinine (μmol/L) | 19.4 ± 3.4 | 20.2 ± 4.1 |
| Total cholesterol (mmol/L) | 2.4 ± 0.2 | 2.3 ± 0.2 |
| Triglyceride (mmol/L) | 0.6 ± 0.1 | 1.0 ± 0.2 |

The method of the invention was capable of simultaneously detecting a plurality of toxicity effects of the secondary effluent of the sewage treatment plant on the liver damage and the metabolic disorder, thereby having high sensitivity and obvious advantage.

In summary, the method for analyzing water toxicity of the invention is capable of comprehensively and accurately assessing toxicity of the water from the underlying genetic information to the final phenotype, simultaneously detecting a plurality of toxicities, and providing a new type of biomarker. Furthermore, the method of the invention has sensitive response to trace toxic substances in the water, thereby being much superior to the conventional toxicity assessment methods.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A method for analyzing water toxicity, the method comprising:
   1) providing model animals, and separating the model animals into a first group and a second group;
   2) providing a water sample comprising organic pollutants and heavy metals as drinking water to the first group; after a first period of time, extracting a first set of RNA samples from livers of the first group, and collecting a first set of blood samples from the first group and centrifuging the first set of blood samples to obtain a first set of serum samples; and
   providing purified water as drinking water to the second group; after a second period of time that is equal to the first period of time, extracting a second group of RNA samples from livers of the second group, and collecting a second set of blood samples from the second group and centrifuging the second set of blood samples to obtain a second set of serum samples;
   3) analyzing the first set of RNA samples by a microarray method to obtain a first transcriptome data; and analyzing the second set of RNA samples by a microarray method to obtain a second transcriptome data;
   4) analyzing the first set of serum samples and the second set of serum samples by nuclear magnetic resonance (NMR) method to yield a first set of NMR spectra and a second set of NMR spectra, respectively;
   5) comparing the first transcriptome data and the second transcriptome data and deeming genes having an expression multiple >2.0 and a false discovery rate (FDR) <0.1 as differentially expressed genes;
   6) integrating the first set of NMR spectra and the second set of NMR spectra to obtain a first integration data and a second integration data, respectively, and analyzing the first integration data and the second integration data by partial least squares discriminant analysis (PLS-DA), and deeming metabolites having variable influence on projection (VIP) >1.0 and FDR <0.01 as differentially expressed metabolites; and
   7) performing biological pathway analyses on the differentially expressed genes and differentially expressed metabolites to identify the biological pathways that are affected by the water sample.

2. The method of claim 1, wherein integrating the first group of NMR spectra and the second group of NMR spectra in 6) is performed with an interval of 0.005 ppm in the first group of NMR spectra and the second group of NMR spectra.

3. The method of claim 1, wherein 7) comprises:
   identifying biological pathways that have a hypergeometric test p <0.05 and contain more than four of the differentially expressed genes as affected transcriptome pathways;
   identifying biological pathways that have a pathway impact (PI) >0.1 as affected metabolite pathways;
   identifying the biological pathways which are both the affected transcriptome pathways and affected metabolite pathways as specific biological processes affected by the water sample, and identifying corresponding differentially expressed genes and metabolites as biomarkers of the water toxicity.

* * * * *